US012128008B2

(12) United States Patent
Grossman et al.

(10) Patent No.: US 12,128,008 B2
(45) Date of Patent: Oct. 29, 2024

(54) NETWORKED CONTAINERS DESIGNED TO PROMOTE COMPLIANCE WITH A MEDICATION REGIMEN

(71) Applicant: Verily Life Sciences LLC, Mountain View, CA (US)

(72) Inventors: Jonathan Grossman, San Francisco, CA (US); Jasper L. Steyn, San Bruno, CA (US)

(73) Assignee: Verily Life Sciences LLC, Dallas, TX (US)

( * ) Notice: Subject to any disclaimer, the term of this patent is extended or adjusted under 35 U.S.C. 154(b) by 136 days.

(21) Appl. No.: 17/792,967

(22) PCT Filed: Jan. 15, 2021

(86) PCT No.: PCT/US2021/013595
§ 371 (c)(1),
(2) Date: Jul. 14, 2022

(87) PCT Pub. No.: WO2021/146531
PCT Pub. Date: Jul. 22, 2021

(65) Prior Publication Data
US 2023/0050270 A1 Feb. 16, 2023

Related U.S. Application Data

(60) Provisional application No. 62/962,784, filed on Jan. 17, 2020.

(51) Int. Cl.
*A61J 7/04* (2006.01)
*A61J 1/03* (2023.01)
(Continued)

(52) U.S. Cl.
CPC .............. *A61J 7/0481* (2013.01); *G08B 5/36* (2013.01); *G16H 20/13* (2018.01); *G16H 40/67* (2018.01);
(Continued)

(58) Field of Classification Search
CPC ......... G16H 20/13; A61J 1/03; A61J 2200/30; A61J 7/0076; A61J 2205/20
See application file for complete search history.

(56) References Cited

U.S. PATENT DOCUMENTS 9,043,015 B2  5/2015  Ratnakar
10,325,479 B2  6/2019  Fateh et al.
(Continued)

OTHER PUBLICATIONS

PCT Search Report and Written Opinion for PCT/2021/013595 mailed Apr. 14, 2021; 9 pages.

*Primary Examiner* — Thomas S McCormack
(74) *Attorney, Agent, or Firm* — Perkins Coie LLP

(57) ABSTRACT

Introduced here are containers designed to promote compliance with regimens for administering the medications stored therein. These containers can facilitate the conveyance of information related to a regimen through the use of a non-written medium. A container may include one or more display elements configured to emit/reflect light to indicate when medication stored in the container should be administered. An example of a display element is a light-emitting diode (LED). Emittance/reflectance of the light by the display element(s) may be governed by a different clock signal than the clock signal used to determine whether doses of medication are due to be administered.

15 Claims, 11 Drawing Sheets

(51) Int. Cl.
 *G08B 5/36* (2006.01)
 *G16H 20/13* (2018.01)
 *G16H 40/67* (2018.01)

(52) U.S. Cl.
 CPC .............. *A61J 1/03* (2013.01); *A61J 2200/30* (2013.01); *A61J 2205/20* (2013.01); *A61J 2205/40* (2013.01)

(56) References Cited

U.S. PATENT DOCUMENTS

| | | | |
|---|---|---|---|
| 2010/0094455 A1* | 4/2010 | Dehlin ................. | A61J 7/0418 |
| | | | 700/232 |
| 2013/0218588 A1* | 8/2013 | Kehr ..................... | G16H 40/63 |
| | | | 705/2 |
| 2017/0095405 A1* | 4/2017 | Afsarifard ............ | A61J 7/0472 |
| 2018/0028406 A1* | 2/2018 | Patton .................. | A61J 7/0069 |
| 2018/0280246 A1 | 10/2018 | Cohen et al. | |

\* cited by examiner

900

901
Examine a dosing schedule associated with a medication stored in a container

902
Determine, based on the dosing schedule, that a dose of medication is due to be administered

903
Cause light to be periodically emitted by an illuminant through an aperture in the container

904
Determine that the dose of medication has been administered

905
Cause light to be continuously emitted by the illuminant through the aperture for a given amount of time

906
Record data indicative of an administration event in a memory

907
Transmit the data to an electronic device

FIGURE 9

NETWORKED CONTAINERS DESIGNED TO
PROMOTE COMPLIANCE WITH A
MEDICATION REGIMEN

CROSS-REFERENCE TO RELATED APPLICATIONS

This application is a national stage entry of International Patent Application No. PCT/US2021/013595, titled "Networked Containers Designed to Promote Compliance with a Medication Regimen" and filed on Jan. 15, 2021, which claims priority to U.S. Provisional Application No. 62/962,784, filed on Jan. 17, 2020, each of which is incorporated herein by reference in its entirety.

TECHNICAL FIELD

Various embodiments concern containers designed to promote compliance with regimens for administering the medications stored therein.

BACKGROUND

A pill organizer (also referred to as a "pill container" or "pill box") is a multi-compartment aid designed to promote compliance with a medication regimen (or simply a "regimen") by storing scheduled doses of one or more medications. Many pill organizers have one or more square-shaped compartments for each day of the week, though other versions have been developed. Some pill organizers have multiple sections corresponding to different times of the day. For instance, a pill organizer could include a first row of seven square-shaped compartments in which medications to be administered in the morning are placed and a second row of seven square-shaped compartments in which medications to be administered in the evening are placed.

Historically, pill organizers have been viewed as a convenient way to reduce the number of errors associated with the administrations of medication(s) required by a regimen. Such errors include administering the wrong dose of a given medication and administering a dose of a given medication at the wrong time. However, evidence of effectiveness of these pill organizers is not strong.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 9 depicts a flow diagram of a process for selectively driving an illuminant to indicate whether medication in a container is due to be administered.

Figure 1:
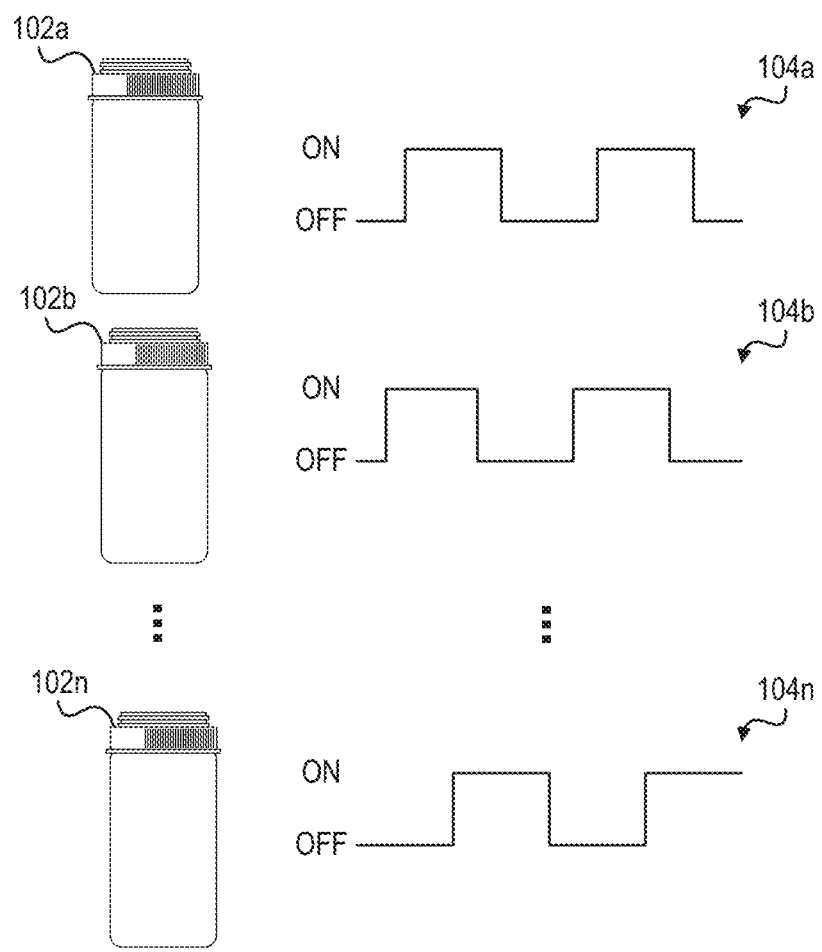
FIG. 1 includes a timing diagram for multiple smart bottles having different medications stored therein that an individual (also referred to as a "patient" or "subject") is responsible for managing.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

To address the drawbacks of conventional pill organizers, entities have begun developing electronic pill bottles designed to alert individuals (also referred to as "patients" or "subjects") when a medication should be taken. Rather than include separate compartments for the doses throughout a given interval of time (e.g., a week), an electronic pill bottle will generally include a single cavity in which a bulk supply of medication is stored. As further discussed below, some models of electronic pill bottles are able to generate notifications to indicate when doses of the medication should be administered. Generally, electronic pill bottles are able to communicate with other electronic devices via a network. Consequently, electronic pill bottles may be referred to as "network-connected bottles" or "smart bottles."

A smart bottle may be designed to communicate, either continually or periodically, with a computer program (e.g., a mobile application) executing on an electronic device. For instance, a smart bottle may be configured to transmit data regarding administrations of medication to a mobile application executing on a mobile phone associated with the individual responsible for administering the medication stored therein. The computer program may promote compliance with a regimen by generating notifications that alert the individual when doses of medication are due to be administered. Some smart bottles promote compliance with the regimen by generating notifications that alert the individual when doses of medication are due to be administered. For instance, a smart bottle may include a light-emitting diode (LED) that emits light on a periodic basis when a dose of medication is due to be administered.

Historically, smart bottles have been designed with several goals in mind. First, a smart bottle should be able to address forgetfulness through on-device notifications (also referred to as "reminders"). Second, a smart bottle should be able to record data related to administrations of medication so that adherence to a regimen can be tracked. However, smart bottles have failed to accomplish these goals in a consistent, predictable, and cost-efficient manner.

Introduced here, therefore, are containers designed to promote compliance with regimens for administering the medications stored therein. These containers can facilitate the conveyance of information related to a regimen through the use of a non-written medium. For example, the containers described herein may be able to clearly communicate when a dose is due to be administered without requiring the individual read the instructions (which may be unclear to untrained individuals), check a dosing schedule, etc.

A container may include a durable housing comprised of a structural body (also referred to as a "container base" or "base") having a cavity defined therein for storing a bulk supply of medication and a cap designed to enclose the cavity when secured to the structural body, an illuminant configured to emit light, a clock module configured to generate a first clock signal, and a processor configured to determine that a dose of the medication is due to be administered based on a comparison of the first clock signal to a dosing schedule and then cause the illuminant to emit light on a periodic basis as a notification that the dose of the medication is due to be administered. Period emittance of the light may be governed by a second clock signal generated independently of the first clock signal. In some embodiments, the second clock signal is generated by a second clock module housed in the container. In such embodiments, the second clock signal is synchronized with a reference clock signal generated by an electronic device whenever the container is communicatively connected to the electronic device. For example, the second clock signal may be synchronized with a reference clock signal generated by a mobile phone associated with the individual responsible for administering the medication whenever the container transmits data to the mobile phone. As another example, the second clock signal may be synchronized with a reference clock signal generated by a docking unit whenever the container is secured to the docking unit. As further discussed below, the second clock signal may govern the periodic emittance of light by multiple containers so that notifications are produced by these containers in unison.

Some embodiments of the container may include multiple illuminants for conveying different types of information. For example, a container may include a first illuminant arranged beneath a first aperture in the structural body and a second illuminant arranged beneath a second aperture in the structural body. The first and second apertures may have different shapes. For example, if the emittance of light by the first illuminant is intended to convey an instruction to administer the medication, the first aperture may be a check-shaped aperture. If the emittance of light by the second illuminant is intended to convey an instruction to refrain from administering the medication, the second aperture may be an x-shaped aperture. Additionally or alternatively, the first and second illuminants may be configured to emit light of different colors. For example, the first illuminant may emit green light to convey an instruction to administer the medication, while the second illuminant may emit red light to convey an instruction to refrain from administering the medication.

Embodiments may be described with reference to particular electronic devices, network configurations, networks, etc. However, those skilled in the art will recognize that the features are equally applicable to other electronic devices, network configurations, networks, etc. Moreover, some tasks may be described as being performed by a container, while other tasks may be described as being performed by another electronic device, such as a mobile phone, docking unit, or a network-accessible server system. Those skilled in the art will recognize that, in many instances, either the container or the electronic device to which it is communicatively connected could perform a specified task.

Embodiments may be described with reference to a container having a particular form. For example, several embodiments are described in the context of a cylindrical bottle having a cavity defined therein for storing a bulk supply of medication in the form of tablets. Those skilled in the art will recognize that these examples are provided for the purpose of illustration only. The technology could be implemented in other forms of medication packaging such as inhalers, syringes, blister packs, etc.

The technology can be embodied using special-purpose hardware (e.g., circuitry), programmable circuitry appropriately programmed with software and/or firmware, or a combination of special-purpose hardware and programmable circuitry. Accordingly, embodiments may include a machine-readable storage medium having instructions that may be used to program an electronic device (e.g., a container) to perform a process for examining a dosing schedule for a medication, determining that a dose of the medication is due to be administered based on a comparison of the dosing schedule with a first clock signal, generating a notification to administer the dose of the medication on a periodic basis as governed by a second clock signal, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Networked Container Overview

Knowing when to administer a dose of medication can be confusing, especially for individuals who are responsible for managing multiple containers of medication, each of which may be associated with a different regimen. For instance, individuals suffering from hypertension are prescribed an average of 7.7 medications, and each of these medications is stored in its own container.

A medical professional, such as a physician or a pharmacist, may recommend that an individual use smart bottles to provide noticeable reminders intended to promote healthy habits. These smart bottles may be recommended by the medical profession as part of an attempt to promote adherence to the regimens associated with the various medications in a more reliable, consistent manner. FIG. 1 includes a timing diagram for multiple smart bottles 102a-n having different medications stored therein that an individual (also referred to as a "patient" or "subject") is responsible for managing. Each smart bottle includes a light-emitting diode (LED) able to emit light as a notification that a dose of the corresponding medication is due to be administered.

Generally, these LEDs emit light on a periodic basis to reduce the amount of power that is consumed during a single dosing window. If an LED were to continuously emit light for the entire dosing window, the smart bottle would likely run out of power before all of the medication had been administered. Periodic emittance of light can be problematic, however, since the multiple smart bottles 102a-n do not communicate with one another. As shown in FIG. 1, misalignment of the notification schedules 104a-n of the smart bottles 102a-n causes light to be emitted in a non-synchronized manner, which can be overwhelming and/or annoying for the individual.

Introduced here, therefore, are containers designed to produce notifications in a synchronized manner so that individuals can consistently administer multiple medications having different dosing schedules in a compliant manner. Such an enhancement is particularly useful to those individuals who are prescribed a regimen that requires the administration of multiple medications stored in separate containers. Moreover, adherence to the regimen may be improved simply by conveying information regarding the dosing schedules of these medications in a more straightforward, comprehensible way.

Figure 2:
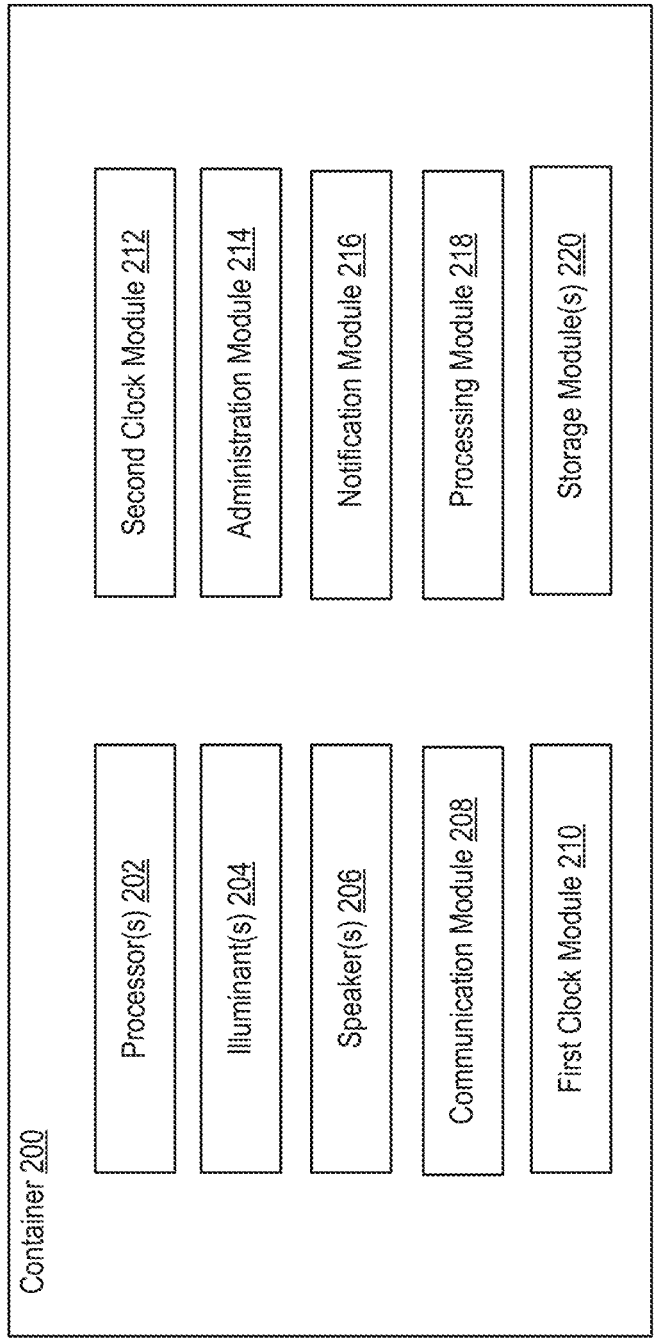
FIG. 2 depicts the high-level architecture of a container able to notify an individual when medication stored therein is due to be administered.

FIG. 2 depicts the high-level architecture of a container 200 able to notify an individual when medication stored therein is due to be administered. The container 200 has a durable housing. As discussed above, the durable housing may include a structural body having a cavity therein for storing a bulk supply of medication (e.g., in the form of pills, aerosol, etc.) and a cap that is detachably connectable to the structural body. When secured to the structural body, the cap encloses the cavity to retain the bulk supply of medication. The structural body may be in the form of a right circular hollow cylinder (also referred to as a "cylindrical shell") defined by two right circular cylinders that share an axis in common and a base perpendicular to the common axis. The base may be located at a first end (also referred to as the "distal end") of the cylindrical shell, and an aperture may be located at a second end (also referred to as the "proximal end") of the cylindrical shell. In such embodiments, the second end may be designed to accommodate a cap. Those skilled in the art will recognize that the components of the container 200 may be housed in the structural body and/or the cap. Thus, unless otherwise noted, the components of the container 200 could be located in either the structural body or the cap.

As shown in FIG. 2, the container 200 may include one or more processors 202, one or more illuminants 204, one or more speakers 206, a communication module 208, a first clock module 210, a second clock module 212, an administration module 214, a notification module 216, a processing module 218, and one or more storage modules 220. In some embodiments a single storage module includes multiple computer programs for performing different operations (e.g., event detection, compression, temporal alignment), while in other embodiments each computer program is hosted in a separate storage module. Embodiments of the container 200 may include some or all of these components, as well as other components not shown here.

The processor(s) 202 can execute modules from instructions stored in the storage module(s) 220, which can be any device or mechanism capable of storing information. For example, the processor(s) 202 may execute the administration module 214 to determine whether a dose of medication is due to be administered. As another example, if the output produced by the administration module 214 indicates that a dose of medication is due to be administered, the processor(s) 202 may execute the notification module 216 to generate a notification to alert an individual to administer the dose.

The illuminant(s) 204 can be driven to emit light on a periodic basis as a notification regarding what action, if any, should be taken with respect to the medication. The illuminant(s) 204 may be able to produce light of different colors. For example, the container 200 may include a first illuminant configured to emit light of a first color, a second illuminant configured to emit light of a second color, etc. Examples of an illuminant are LEDs, organic LEDs, liquid crystal elements, and electrophoretic elements. An LED is a two-lead illuminant that is generally comprised of an inorganic semiconductor material. Examples of available colors of LEDs include red, orange, yellow, green, blue, and violet. The components needed to operate the illuminant(s) 204 may connected to illuminant(s) 204 via conductive wires running through the container 200. Examples of operating components include drivers, processor(s) 202, power sources (e.g., a battery), etc.

While embodiments may be described in the context of LEDs, the technology is similarly applicable to other types of display elements (also referred to as "information display units" or "information display modules"). For example, the container 200 may include one or more reflective components that create visual notifications by reflecting ambient light in addition to, or instead of, emissive components that create visual notifications by emitting light. Examples of reflective components include electrophoretic elements and liquid crystal display elements. Moreover, embodiments of the container 200 include other display elements in addition to, or instead of, the illuminant(s) 204. For example, the container 200 may include a liquid crystal display, an organic LED display, an electrophoretic display, etc. In such embodiments, information may be presented (e.g., periodically flashed) on the display element in concert with the display elements of other nearby containers. Thus, the container 200 may include one or more display elements that are configured to emit or reflect light.

The speaker(s) 206 can convert an electrical signal received from the processor(s) 202 into acoustic sound waves (or simply "sound") that are audible to the individual. The speaker(s) 206 may be driven to emit sound on a periodic basis as a notification regarding what action, if any, should be taken with respect to the medication. For example, a tone or an utterance (e.g., "Administer medication now.") may be emitted from the speaker(s) 206 in response to determining that a dose of the medication is due to be administered.

Some embodiments of the container 200 are designed to only produce visual notifications, and thus may include the illuminant(s) 204 but not the speaker(s) 206. Other embodiments of the container 200 are designed to only produce audible notifications, and thus may include the speaker(s) 206 but not the illuminant(s) 204. A container 200 may also be able to produce tactile notifications in addition to, or instead of, visual and audible notifications. Such embodiments of the container 200 may include a feedback mechanism, such as an eccentric rotating mass (ERM) actuator, driven by a haptic engine executable by the processor(s) 202.

The communication module 208 can manage communications between various components of the container 200. The communication module 208 can also manage communications between the container 200 and another electronic device. For example, the communication module 208 may facilitate communication with a mobile phone, wireless access point (WAP), network-accessible server system, etc. As further discussed with respect to FIGS. 3-5, the communication module 208 may transmit data generated by the container 200 to a network-accessible server system that includes one or more computer servers for further review. Additionally or alternatively, the communication module 208 can be configured to transmit data generated by the container 200 to another electronic device. The other electronic device may be associated with the individual, a medical professional (e.g., a physician, pharmacist, nurse, or researcher), medical enterprise/location (e.g., a hospital, pharmacy, or nursing home), etc. For example, the communication module 208 may transmit data to a mobile phone responsible for processing the data and/or forwarding the data to the network-accessible server system.

The first clock module 210 is responsible for issuing a first steady, high-frequency clock signal that can be used to determine whether a dose of medication is due to be administered. Meanwhile, the second clock module 212 is responsible for issuing a second steady, high-frequency clock signal that may govern the periodic emittance of notifications. As further discussed below, the first and second clock signals are generated independently of one another. The first and second clock modules 210, 212 may take the form of separate integrated circuits on the printed circuit board of the container 200.

The administration module 214 can be configured to examine a dosing schedule for the medication stored in the container 200 and then determine whether a dose of the medication is due to be administered based on a comparison of the dosing schedule and the first clock signal generated by the first clock module 210. More specifically, the administration module 214 can examine the dosing schedule to identify the times at which administration events are scheduled to occur and then determine, based on the first clock signal generated by the first clock module 210, which administration events, if any, are due to be completed. In some embodiments the dosing schedule is stored in a local memory (e.g., one of the storage module(s) 220), while in other embodiments the dosing schedule is stored in a remote memory (e.g., accessible to the communication module 208 across a network).

If the administration module 214 determines that a dose of medication is due to be administered, the notification module 216 can cause a notification to be generated on a periodic basis as an alert. More specifically, the notification module 216 can create a signal for driving at least one indicator to periodically produce the notification. Examples of indicators include the illuminant(s) 204, speaker(s) 206, and feedback mechanisms. Thus, the notification module 216 may cause the illuminant(s) 204 to periodically emit pulses of light as the notification. Additionally or alternatively, the notification module 216 may cause the speaker(s) 206 to periodically emit sounds, such as tones or melodies, as the notification. Periodic generation of the notification may be governed by the second clock signal generated by the second clock module 212.

The processing module 218 can apply one or more operations to data regarding adherence to the dosing regimen that is generated by the container 200. Generally, the container 200 will produce data over time that indicates when the individual administered doses of medication. For example, some embodiments of the container 200 include a microphone able to record speech uttered by the individual. In such embodiments, the processing module 218 may be able to infer when an administration event occurred based on content and/or context of these utterances (e.g., the individual may be prompted to audibly confirm that a dose was administered). As another example, the processing module 218 could infer that an administration event occurred based on an analysis of movement data generated by an inertial measurement unit (IMU) that includes an accelerometer, gyroscope, etc. As another example, the processing module 218 could infer that an administration event occurred based on an analysis of pressure data generated by a pressure sensor located beneath the cavity in the structural body in which the bulk supply of medication is stored. As another example, the processing module 218 could infer that an administration event occurred based on an analysis of tactile data representative of interactions with a mechanical button accessible through the structural body of the container 200.

The container 200 may be configured to continually or periodically transmit data to another electronic device. In some embodiments, the container 200 streams data to the other electronic device in real time. In such embodiments, the container 200 may transmit data to the other electronic device so long as the container 200 remains communicatively connected to the other electronic device. The other electronic device may be a mobile phone, docking unit, mobile computer cart (also referred to as a "hospital computer cart," "medical computer cart," or "mobile workstation"), wireless access point (WAP), computer server, etc.

In other embodiments, the container 200 uploads data to the other electronic device on a periodic basis. The container 200 may upload data hourly, daily, weekly, etc. Alternatively, the container 200 may transmit data to the other electronic device in response to receiving an instruction to do so. For example, a computer program executing on a mobile phone may transmit an instruction to the container 200 to provide data related to administration events responsive to determining that a communication channel has been established between the mobile phone and the container 200.

Synchronized Indicators for Promoting Adherence

Figure 3:
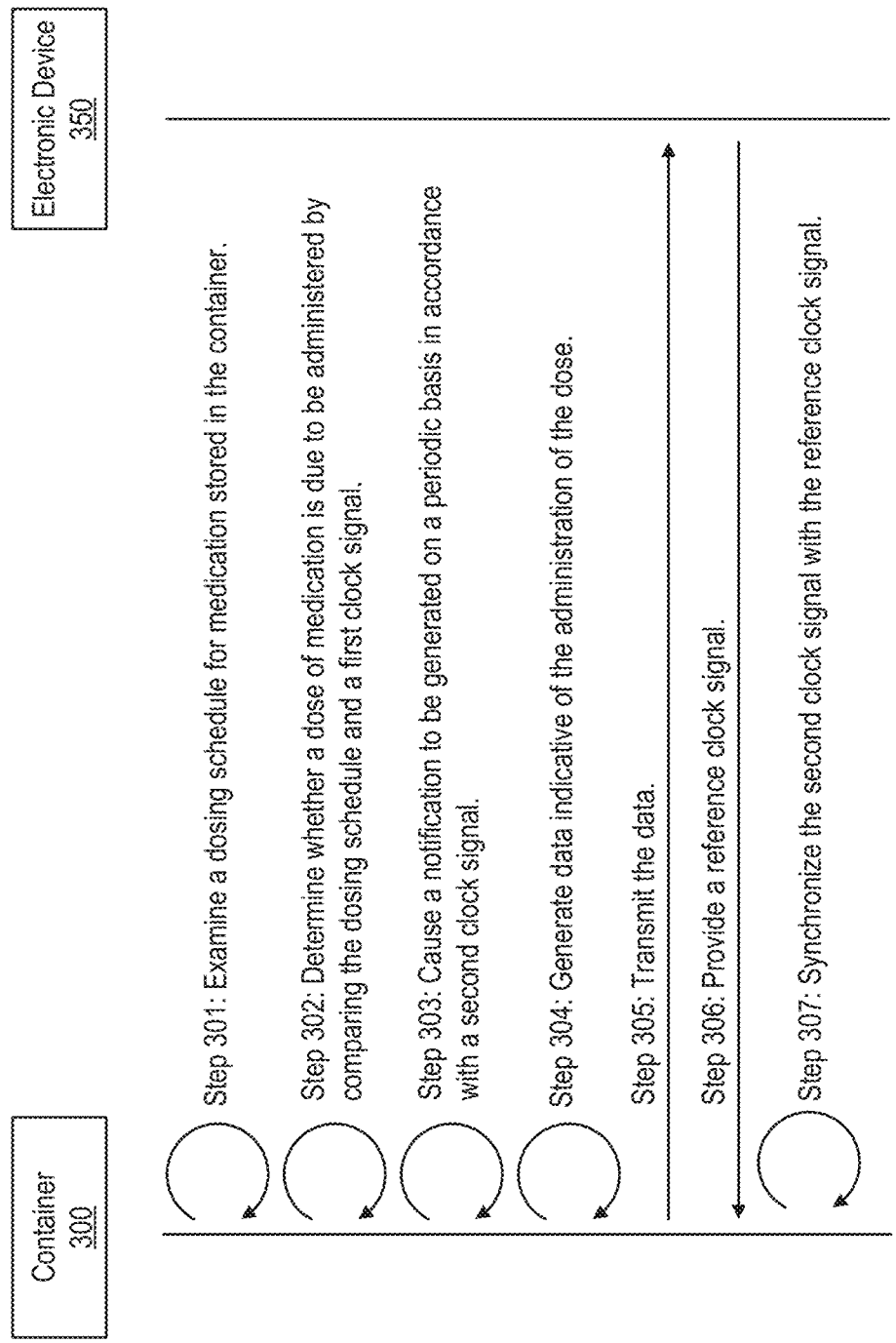
FIG. 3 includes a high-level illustration of communications between a container that includes a bulk supply of medication and an electronic device that is responsible for processing, examining, or forwarding data generated by the container so that compliance with a regimen can be determined.

FIG. 3 includes a high-level illustration of communications between a container 300 (e.g., container 200 of FIG. 2) that includes a bulk supply of medication and an electronic device 350 that is responsible for processing, examining, or forwarding data generated by the container 300 so that compliance with a regimen can be determined. One example of an electronic device 350 is a mobile phone associated with the individual responsible for administering the medication. Another example of an electronic device 350 is a base station (also referred to as a "hub unit") capable of relaying data between the container 300 and a network-accessible server system.

Initially, the container 300 can examine a dosing schedule for a medication stored therein (step 301). In some embodiments, the dosing schedule is loaded into local memory by the individual responsible for administering the medication or a medical professional. In other embodiments, the dosing schedule is retrieved from a remote memory during a configuration process. For example, the dosing schedule may be retrieved from a network-accessible storage medium associated with a medical enterprise such as a hospital or pharmacy when the medication is loaded into the container 300.

Then, the container 300 can determine whether a dose of medication is due to be administered by comparing the dosing schedule and a first clock signal generated by a first clock module (step 302). In response to determining that a dose of medication is due to be administered, the container 300 can cause a notification to be generated on a periodic basis in accordance with a second clock signal generated by a second clock module (step 303). The purpose of the first clock module is to generate an output that can be used to track the dosing schedule of the medication, while the purpose of the second clock module is to generate an output that can be used to regulate the notification schedule of an indicator. Examples of indicators include the illuminants operable to produce visual notifications, speakers operable to produce audible notifications, and feedback mechanisms operable to produce tactile notifications. Accordingly, the container 300 may be able to drive an illuminant such that light is emitted (e.g., by flashing or pulsing) on a periodic basis as a visual notification.

The container 300 may be able to generate administration data indicative of administrations of doses of medication (step 304). This administration data may be useful in determining the degree to which the individual is complying with a regimen requiring administration of the medication. For example, the administration data may provide insights into the compliance of individual administration events (e.g., whether the individual skipped a scheduled dose) or series of administration events (e.g., whether the individual is routinely late in administering doses scheduled for the morning).

Administration data may comprise, or be derived from, various types of data generated by components of the container 300. For example, the container 300 may infer that administration events have occurred based on an analysis of audio data generated by a microphone able to record sounds in the ambient environment. As another example, the container 300 may infer that administration events have occurred based on an analysis of movement data generated by an IMU whose movement is representative of movement of the container 300. As another example, the container 300 may infer that administration events have occurred based on an analysis of pressure data generated by a pressure sensor located beneath the cavity in which medication is stored or beneath the lid that must be removed to access the cavity. As another example, the container 300 may infer that administration events have occurred based on an analysis of tactile data representative of interactions with a mechanical button accessible through the structural body of the container.

The container 300 may transmit the administration data to the electronic device 350 for further review (step 305). For example, a processor responsible for generating/processing the administration data may forward the administration data to a transmitter for modulation onto an antenna for wireless transmission to the electronic device 350. The transmitter may be part of a transceiver capable of transmitting communications to, and receiving communications from, the electronic device 350.

Each time the container 300 transmits administration data to the electronic device 350, the electronic device 350 may provide a reference clock signal to the container 300 (step 306). Generally, the reference clock signal is generated by a reference clock module housed in the electronic device 350. Thereafter, the container 300 may synchronize the second clock signal with the reference clock signal (step 307). While the second clock signal would normally experience some temporal drift with respect to the reference clock signal over extended intervals of time (e.g., days, weeks, or months), consistent performance of steps 305-307 ensures that notifications generated by the container 300 are governed by a second clock signal that is tightly coupled to the reference clock signal. For instance, steps 305-307 may be performed whenever the container 300 and electronic device 350 are communicatively connected to one another. In some embodiments, the frequency with which the second clock signal is synchronized with the reference clock signal is based on the fidelity of the second clock module (e.g., as determined based on error rate) and the optical resolution. For example, synchronization may occur less frequently if the notification is generated every ten seconds rather than every two seconds.

In some embodiments, the electronic device 350 forwards at least some of the data acquired from the container 300 to a network-accessible server system comprised of one or more computer servers. For example, a computer program executing on the electronic device 350 may forward the data to a computer server via the Internet for further review.

As discussed above, the container 300 may be one of multiple containers that the individual is responsible for managing. Each container may independently perform the process shown in FIG. 3 such that a notification is generated on a periodic basis if a dose of the corresponding medication is due to be administered. However, because periodic generation of the notification by each container is governed by a clock signal that is tightly coupled to the same reference clock signal, these notifications will be generated in unison.

For example, assume that an individual is responsible for monitoring five containers, two of which include medications to be administered at 9 AM and three of which include medications to be administered at 6 PM. Each evening at 6 PM, three of the containers will generate notifications in synchronization with one another. If the individual fails to administer those three medications, the next morning at 9 AM all five containers will generate notifications in synchronization with one another.

Figure 4:
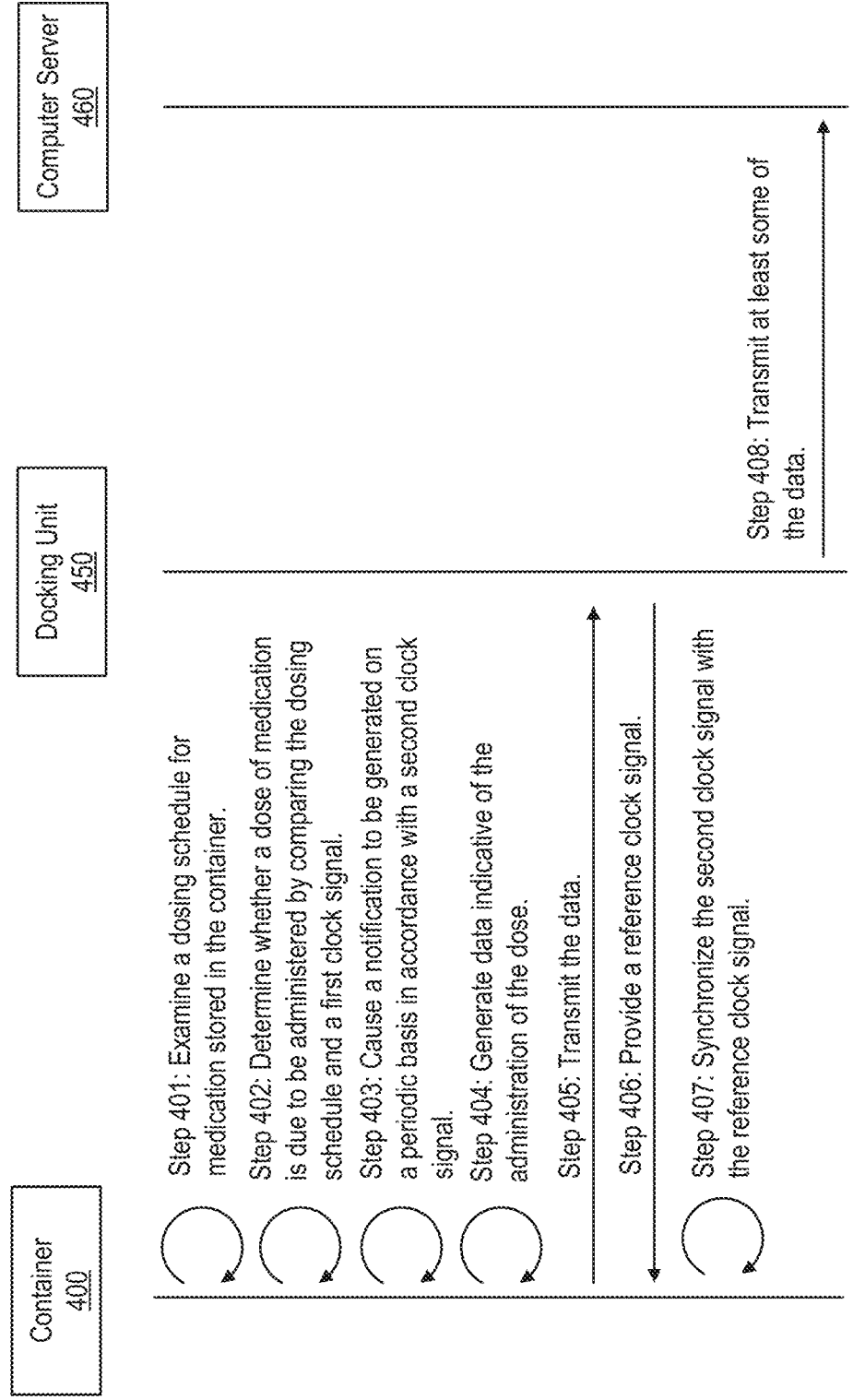
FIG. 4 includes a high-level illustration of communications between a container that includes a bulk supply of medicine and a docking unit to which the container can be secured.

FIG. 4 includes a high-level illustration of communications between a container 400 that includes a bulk supply of medicine and a docking unit 450 to which the container 400 can be secured. The docking unit 450 may include a durable housing with multiple cavities defined therein for accommodating containers. For example, the structural body of the docking unit 450 may include a series of circular slots designed to accommodate the cylindrical shells of containers, rectangular slots designed to accommodate the rectangular shells of containers, etc.

When the container 400 is secured in one of these cavities, power and/or data transfer may be permitted to occur between the container 400 and the docking unit 450. For example, the container 400 may include one or more electrical contacts (e.g., pin terminals) that are able to physically connect one or more corresponding electrical contacts of the docking unit 450. As another example, the container 400 may include integrated circuits (also referred to as "chips") that are able to facilitate the wireless transfer of power and/or data with the docking unit 450.

Steps 401-407 may be substantially similar to steps 301-307 of FIG. 3. Here, however, the docking unit 450 transmits at least some of the data acquired from the container 400 to a computer server 460 for further review (step 408). In FIG. 4, the reference clock signal provided to the container 400 is generated by a reference clock module that is located in the docking unit 450. However, the reference clock signal provided to the container 400 could be generated by a reference clock module that is located in the computer server 460. Alternatively, the reference clock signal provided to the container 400 could be generated by a reference clock module that is located in another container secured to the docking unit 450. In these embodiments, the docking unit 450 may forward the reference clock signal (or data indicative of the reference clock signal) to the container 400 upon receiving it from the computer server 460 or the other container. Accordingly, in some embodiments, the docking unit 450 relays the reference clock signal rather than generating it.

As shown in step 406 of FIG. 4, the docking unit 450 can provide the reference clock signal to the container 400. In some embodiments, this reference clock signal is synchronized with another reference clock signal. For example, the computer server 460 may provide a first reference clock signal to the docking unit 450, and the docking unit 450 may provide a second reference clock signal based on the first reference clock signal to the container 400. Such an arrangement may help the container 400 schedule notifications around daylight savings time, changes in the time zone, etc.

Figure 5:
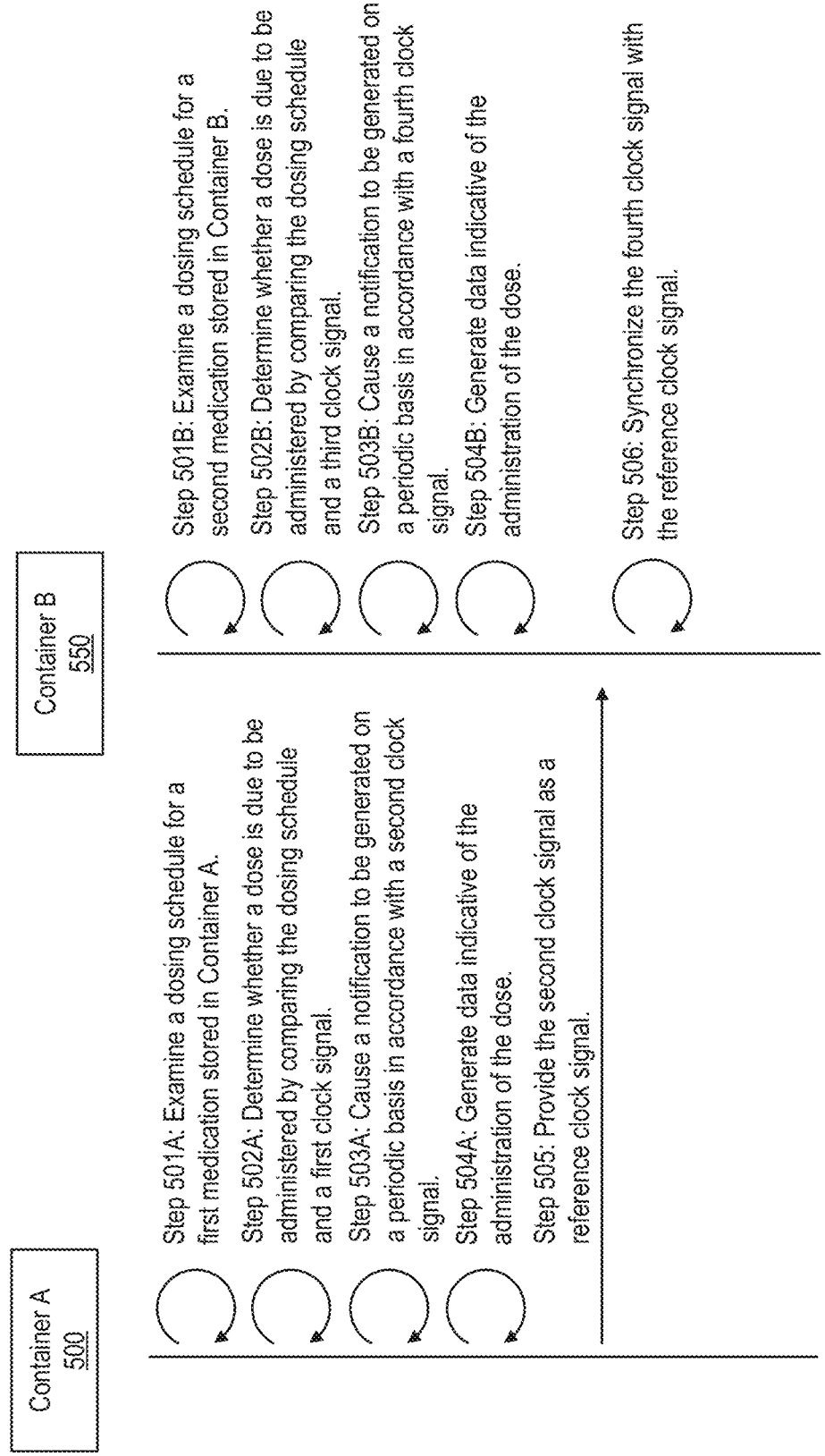
FIG. 5 includes a high-level illustration of communications between a first container that includes a bulk supply of a first medication and a second container that includes a bulk supply of a second medication.

FIG. 5 includes a high-level illustration of communications between a first container 500 that includes a bulk supply of a first medication and a second container 550 that includes a bulk supply of a second medication. Steps 501-504 are substantially similar to steps 401-404 of FIG. 4. Here, however, the first and second containers 500, 550 can execute these steps independently in parallel. Thus, the first container 500 can execute steps 501A-504A to promote compliance with a first regimen associated with the first medication, while the second container 550 can execute steps 501B-504B to promote compliance with a second regimen associated with the second medication.

In this arrangement, the first and second containers 500, 550 are able to communicate directly with one another. Accordingly, one of the containers may acting as a leader container by providing the reference clock signal to be used by the other container to periodically generate notifications. Here, for example, the first container 500 provides the second clock signal to the second container 550 as a reference signal (step 505). This may be done periodically (e.g., every several minutes, hours, days, or weeks). The second container 550 can then synchronize the fourth clock signal with the reference signal (step 506), so that the notifications are generated by the first and second containers 500, 550 in unison.

Generally, the first and second containers 500, 550 are configured to transmit adherence data, either periodically or continually, to another electronic device even though the reference clock signal is supplied by one of the containers. For example, the first and second containers 500, 550 may transmit adherence data to a mobile phone, hub unit, or computer server for further review. Those skilled in the art will recognize that the second container 550 may be one of multiple containers to which the first container 500 provides the second clock signal as a reference clock signal. Each of these containers may separately communicate administration data to the other electronic device, even though synchronization is managed by the first container 500.

Those skilled in the art will recognize that the communications of FIG. 5 are discussed in the context of a pair of containers for the purpose of illustration. A patient could be responsible for managing any number of containers, and these containers could communicate with one another in various ways. For example, in some embodiments each container is able to communicate with all other containers (e.g., as part of a mesh network), while in other embodiments each container communicates with a single container (e.g., a leader in a hub-and-spoke network).

Communication Environment

Figure 6:
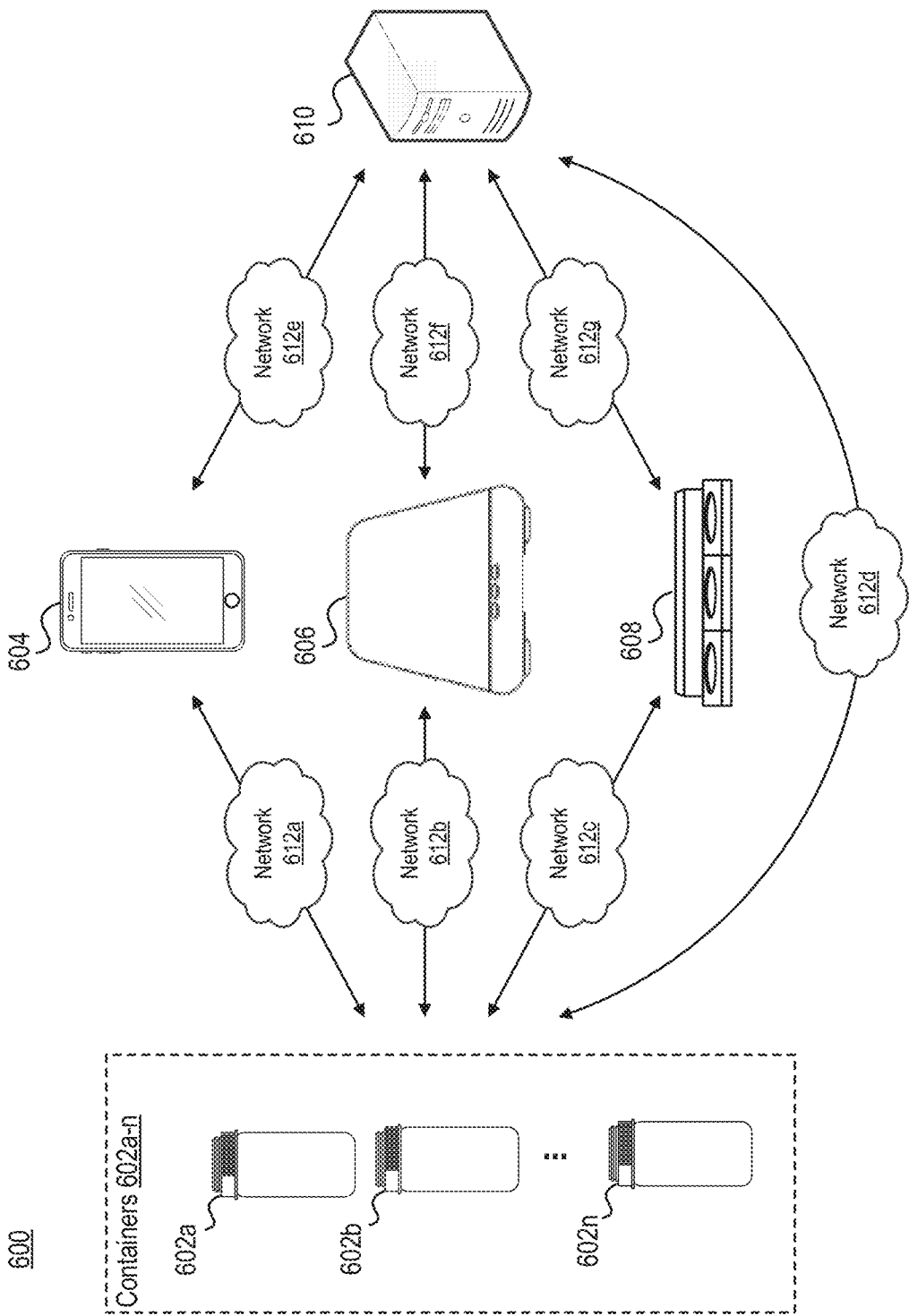
FIG. 6 depicts an example of a communication environment that includes multiple containers having medications stored therein.

FIG. 6 depicts an example of a communication environment 600 that includes multiple containers 602a-n having medications stored therein. As discussed above, the containers 602a-n can be configured to communicate with one or more electronic devices. For example, the containers 602a-n may transmit data to a given electronic device, receive a reference clock signal from a given electronic device, etc. Examples of electronic devices include mobile phones 604, hub units 606, docking units 608, and computer servers 610. The containers 602a-n and electronic device(s) may collectively be referred to as the "networked devices."

The networked devices can be connected to one another via one or more networks 612a-g. The network(s) 612a-g can include personal area networks (PANs), local area networks (LANs), wide area networks (WANs), metropolitan area networks (MANs), cellular networks, the Internet, etc. Additionally or alternatively, the networked devices may communicate with one another over a short-range communication protocol, such as Bluetooth®, near-field communication (NFC), Wi-Fi, ZigBee®, LoRa®, another commercial point-to-point protocol, or a proprietary point-to-point protocol. For example, each container 602a-n may include a Bluetooth® Low Energy chipset, a Wi-Fi® chipset, etc. In some embodiments, the containers 602a-n are communicatively coupled to the mobile phone 604 via separate Bluetooth® communication channels, and the mobile phone 604 is communicatively coupled to the computer server 610 via a Wi-Fi communication channel or a cellular communication channel.

Embodiments of the communication environment 600 may include some or all of the networked devices. For example, some embodiments of the communication environment 600 include containers 602a-n and a single electronic device (e.g., the mobile phone 604) that is responsible for examining adherence data generated by the containers 602a-n. Moreover, the single electronic device may be responsible for providing a reference clock signal as discussed above with respect to FIG. 3. As another example, some embodiments of the communication environment 600 include containers 602a-n and a computer server 610 on which adherence data is stored for subsequent review. In such embodiments, the reference clock signal may be provided by one of the containers 602a-n as discussed above with respect to FIG. 5.

Creating and Modifying Existing Collections of Containers

Regimens may change over time. For example, if a new medication is prescribed to be administered as part of a regimen, an individual may wish to add a new container to an existing collection of containers that are already synchronized with one another. The way in which the new container is added to the existing collection may depend on how those containers communicate with one another.

In some embodiments, the existing collection of containers can directly communicate with one another. As discussed above, in some embodiments each container may be able to communicate with all other containers in the existing collection (e.g., as part of a mesh network), while in other embodiments each container may communicate with a single container in the existing collection (e.g., a leader in a hub-and-spoke network). Regardless of the network form, each container may be responsible for harboring information that indicates it is part of the existing collection. For example, each container may store a synchronization code in its memory that identifies the existing collection. An example of a synchronization code is a computer-readable code that uniquely identifies the existing collection. In some embodiments the synchronization code is encrypted, while in other embodiments the synchronization code is not encrypted.

To link a new container with the existing collection of containers, the new container may be brought within proximity of one of the containers (referred to as the "existing container") in the existing collection. For example, an individual may tap the existing container with the new container. As another example, at least some containers in the existing collection may be operable to continually/periodically scan for nearby containers within a given proximity (e.g., based on communication protocol). Such action may prompt the new and existing containers to communicate with one another. For example, the new and existing containers may exchange messages that include the synchronization code, if any, stored in the respective memories.

Responsive to a determination that the new container does not include a synchronization code in its memory, the synchronization code associated with the existing collection can be transmitted from the existing container to the new container. In some embodiments, the existing container proactively sends the synchronization code responsive to determining that the message received from the new container does not include a synchronization code. In other embodiments, the new container proactively requests that the synchronization code be provided by the existing container responsive to determining that no synchronization code is stored in its memory.

Those skilled in the art will recognize that responsibilities could be transferred between containers in a similar manner. As discussed above with respect to FIG. 5, a container may act as a leader container for the existing collection (e.g., by providing the reference clock signal to be used to periodically generate notifications). An individual could transfer these leader responsibilities to another container by bringing these containers within proximity of one another. For example, the individual may tap these containers together to transfer leader responsibilities upon discovering that the current leader container does not include any more medication.

In other embodiments, the existing collection of containers indirectly communicate with one another via an electronic device. Examples of electronic devices include mobile phones, hub units, docking units, and computer servers. In such embodiments, the electronic device may include an identifier associated with each container that is part of the existing collection. For example, a mobile phone may include a mobile application able to identify, and communicate with, each container that is part of the existing collection. The individual may be able to manage the existing collection of containers through the mobile application. For example, the mobile application may permit the individual to add containers, remove containers, etc. When a container is added to a collection, the mobile application may transmit an instruction to the container to add a new synchronization code to its memory. When a container is removed from a collection, the mobile application may transmit an instruction to the container to remove the existing synchronization code from its memory.

Multiple collections of containers may exist on a single network in some instances. For example, a husband may be responsible for managing a first collection of containers, and a wife may be responsible for managing a second collection of containers. As discussed above, these collections of containers can be distinguished from one another using synchronization codes. For example, each container in the first collection of containers may include, or be associated with, a first synchronization code, while each container in the second collection of containers may include, or be associated with, a second synchronization code. Such an arrangement ensures that the containers in the first collection are synchronized with one another independent of the containers in the second collection that are synchronized with one another.

Discrete Indicators for Promoting Adherence

Several entities have developed smart bottles with LEDs that emit light to indicate when doses of medication should be administered. However, many individuals find that these visual notifications are difficult to interpret. For instance, it may be unclear how the strength and/or frequency of flashes of light emitted by a smart bottle are related to administrations of medication. This is especially true if these LEDs are also used to communicate other information, such as power level, connectivity status, etc.

Figure 7:
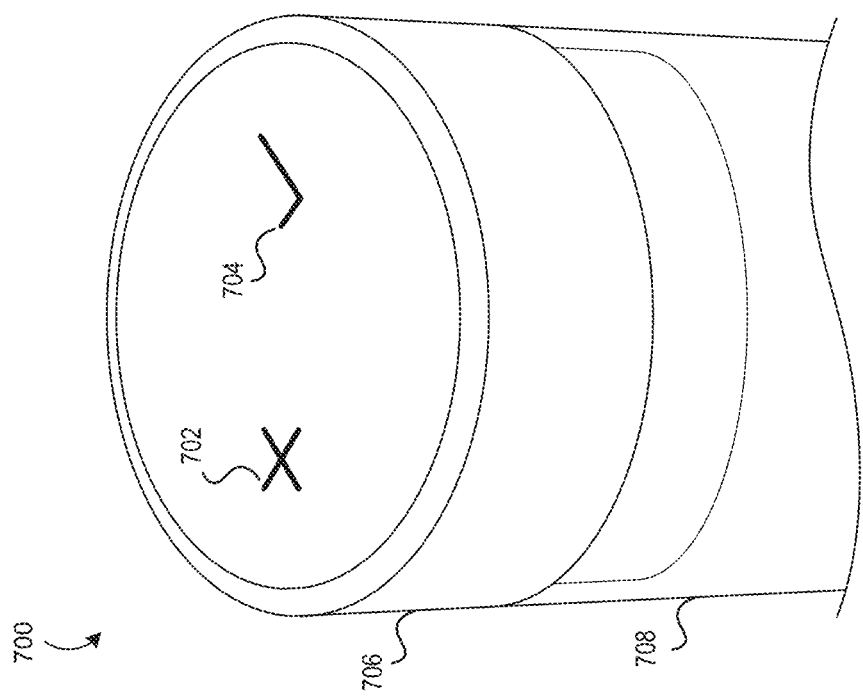
FIG. 7 depicts an example of a container that includes multiple illuminants for conveying different types of information.

Introduced here are containers that address this issue by arranging illuminants beneath apertures in the structural housing that are designed to provide context for visual notifications. FIG. 7 depicts an example of a container 700 that includes multiple illuminants for conveying different types of information. Here, the container 700 includes a first illuminant arranged beneath a first aperture 702 and a second illuminant arranged beneath a second aperture 704. While these apertures 702, 704 are formed in the lid 706, those skilled in the art will recognize that the first and second apertures 702, 704 could be formed in the structural body 708 of the container 700. As discussed above, while various features may be described in the context of illuminants, those skilled in the art will recognize that similar features may be exhibited by other types of display elements. These display elements could be either segmented or matrixed.

The first and second apertures 702, 704 enable the container 700 to utilize visual notifications in a more focused way. Here, for example, the first aperture 702 is an x-shaped aperture and the second aperture 704 is a check-shaped aperture. An x-shaped glowing icon will be created when light is emitted by the first illuminant, and a check-shaped glowing icon will be created when light is emitted by the second illuminant. As further discussed with respect to FIG. 8, these glowing icons can be created in different patterns to indicate to an individual whether a dose of medication should be administered in accordance with a dosing schedule. The dosing schedule may be pre-programmed (e.g., by a medical professional at a medical enterprise such as a pharmacy, or by the individual through a computer program executing on an electronic device that is communicatively connected to the container 700).

Figure 8:
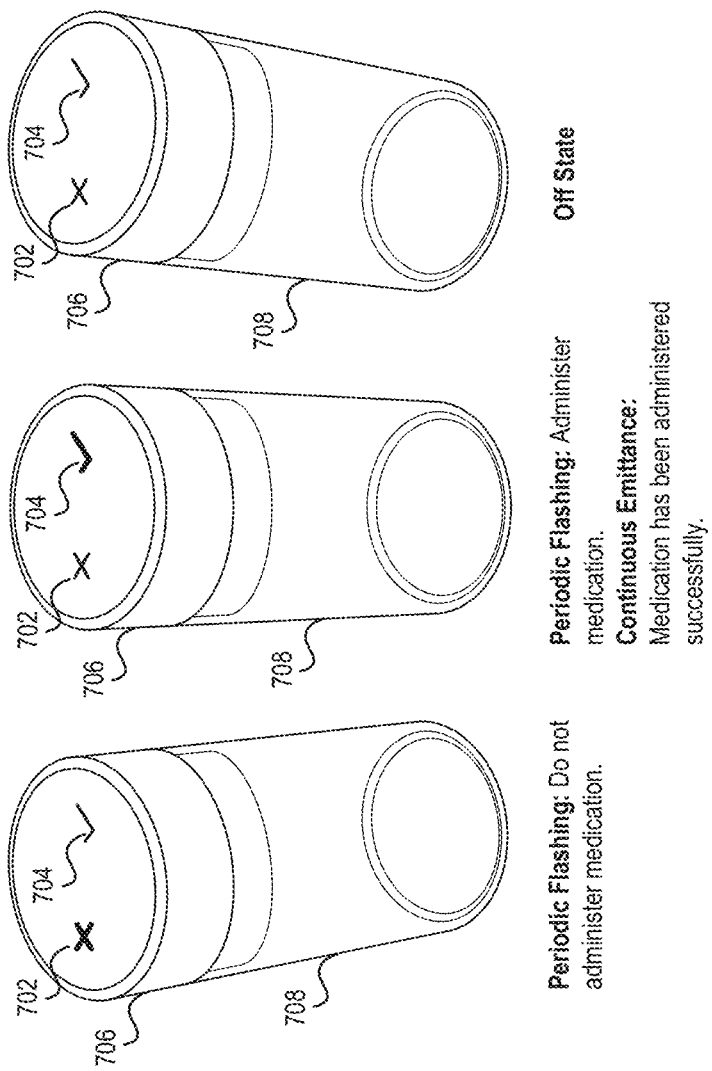
FIG. 8 illustrates how a container may drive the illuminant(s) positioned beneath each aperture to convey information regarding the regimen for the medication stored therein.

FIG. 8 illustrates how the container 700 may drive the illuminant(s) positioned beneath each aperture to convey information regarding the regimen for the medication stored therein. The container 700 may drive the first illuminant so that the first aperture 702 intermittently flashes (e.g., every 15, 30, 60, or 120 seconds) in response to determining that no doses of the medication are due to be administered. The duration of each flash may be based on the amount of power available to the container 700. For example, if the container 700 includes a relatively low number of doses of medication, the flashes may be longer in duration since the medication will be consumed in a short amount of time. Additionally or alternatively, the duration of each flash may be based on the dominant wavelength of the light emitted by the first illuminant. For example, illuminants configured to emit red or green light may produce longer flashes since those illuminants consume less power than illuminants configured to emit blue or purple light.

The container 700 may drive the second illuminant so that the second aperture 704 continually flashes (e.g., every 3, 5, 10, or 30 seconds) in response to determining that a dose of the medication is due to be administered. To gain the attention of the individual, the second aperture 704 may flash more frequently than the first aperture 702. The second aperture 704 may continue flashing until the individual opens the lid 706 to access the bulk supply of medication. Each time the lid 706 is opened may be recorded by the container 700 as an administration event.

When the container 700 determines that a dose of medication has been administered (e.g., based on a discovery that the lid 706 has been removed from and/or secured to the structural body 708), the container 700 may drive the second illuminant so that the second aperture 704 is continuously illuminated for an interval of time (e.g., 3, 5, 10, or 30 seconds).

Those skilled in the art will recognize that the shapes of the apertures shown here have been selected for the purpose of illustration. Apertures having different shapes may be desirable in certain circumstances. For example, the container 700 may include a thumbs-down aperture instead of the x-shaped aperture and a thumbs-up aperture instead of the check-shaped aperture. As another example, the container 700 may include circular apertures instead of the x- and check-shaped apertures.

Some embodiments of the container 700 include more than two apertures. For example, the container 700 may include a third aperture located above a third illuminant that can be driven to indicate when a dose has been completed successfully or when adherence data has been uploaded successfully. The third aperture may have a different shape than the first and second apertures 702, 704. For example, the third aperture may be an annulus-shaped aperture (also referred to as a "ring-shaped aperture"). Moreover, the third illuminant may be configured to emit a different color of light than the first and second illuminants. For example, the first illuminant may emit red light, the second illuminant may emit green light, and the third illuminant may emit blue light.

Some embodiments of the container 700 include a single aperture. For example, the container 700 may include the second aperture 704 but not the first aperture 702. In such embodiments, the container 700 can still indicate to the individual when a dose of medication should be administered. Though such embodiments of the container 700 cannot explicitly indicate when a dose of medication should not be administered, the container 700 can implicitly indicate when a dose of medication should not be administered by not emitting light through the second aperture 704.

As discussed above, one drawback of visual notifications is that illuminants tend to consume larger amounts of power than speakers capable of generating audible notifications and feedback mechanisms capable of generating tactile notifications. One option for addressing this drawback is to ensure that the illuminants emit light only when the individual responsible for administering the medication is nearby. The container 700 may be able to establish the proximity of the individual in several different ways.

For example, the container 700 may include a proximity sensor configured to generate data representative of a series of proximity measurements indicative of proximity of the individual. The proximity sensor may emit an electromagnetic field or a beam of electromagnetic radiation (e.g., infrared radiation) and then look for changes in the field or return beam. In such embodiments, the container 700 may cause the appropriate illuminant to emit light only upon determining, based on the data, that the individual is within a given proximity.

As another example, the container 700 may include an accelerometer configured to generate data representative of a series of measurements indicative of acceleration of the container. In such embodiments, the container 700 may cause the appropriate illuminant to emit light only upon inferring, based on the data, that the individual has interacted with the container within a given amount of time. The inference may be based on at least one acceleration measurement that exceeds a predetermined value or a series of acceleration measurements that match a pattern-defining parameter.

As another example, the container 700 may include a mechanical button accessible through its structural body. Data indicative of events involving interactions with the mechanical button can be generated, for example, by a pressure sensor positioned beneath the mechanical button. In such embodiments, the container 700 may cause the appropriate illuminant to emit light only upon determining, based on the data, that the individual has interacted with the mechanical button within a given amount of time.

As another example, the container 700 may include a microphone configured to generate data indicative of sounds external to its structural body. In such embodiments, the container 700 may cause the appropriate illuminant to emit light only upon inferring, based on the data, that the individual has been located in proximity to the container 700 within a given amount of time. The inference may be based on a presence of a sound representative of the individual. For instance, the container 700 may be able to detect the presence of a keyword, or the container 700 may be able to identify an audible characteristic (e.g., frequency or cadence) that is representative of the individual.

As another example, the container 700 may include a communication module configured to communicate with an electronic device associated with the individual. For instance, the container 700 may include a Bluetooth® Low Energy chipset or a Wi-Fi® chipset. In such embodiments, the container 700 may cause the appropriate illuminant to emit light only upon inferring that the individual is within a given proximity. Such an inference may be based on whether the communication module is presently connected to the electronic device.

FIG. 9 depicts a flow diagram of a process 900 for selectively driving an illuminant to indicate whether medication in a container is due to be administered. Initially, the container examines a dosing schedule associated with the medication stored therein (step 901). In some embodiments, the dosing schedule is loaded into local memory by the individual responsible for administering the medication or a medical professional. In other embodiments, the dosing schedule is retrieved from a remote memory during a configuration process. For example, the dosing schedule may be retrieved from a network-accessible storage medium associated with a medical enterprise such as a hospital or pharmacy when the medication is loaded into the container.

Then, the container can determine whether a dose of medication is due to be administered. For example, the container may accomplish this by comparing the dosing schedule and a clock signal generated by a clock module, as discussed above. In response to determining that a dose of medication is due to be administered (step 902), the container can cause light to be periodically emitted by an illuminant through an aperture in the container (step 903). In particular, the container can cause a control signal to be transmitted to the illuminant that causes light to be emitted on a periodic basis. In some embodiments the aperture is formed in the cap of the container, while in other embodiments the aperture is formed in the structural body of the container.

Thereafter, the container may determine that the dose of medication has been administered (step 904). For example, the container may infer that the medication has been administered based on the presence of an utterance (e.g., "medication administered" or "dose administered") in audio data generated by a microphone. As another example, the container may infer that the medication has been administered based on analysis of movement data generated by an IMU. As another example, the container may infer that the medication has been administered based on an analysis of pressure data generated by a pressure sensor located beneath the cavity in which the medication is stored.

The container may cause light to be continuously emitted by the illuminant through the aperture for a given amount of time in response to determining that the dose of medication has been administered (step 905). For example, the container may drive the illuminant such that light is continuously emitted for 5-30 seconds to indicate that the administration event has been acknowledged. In some embodiments, the container records data indicative of the administration event in a memory (step 906). For example, the container may store the data in the same memory as the dosing schedule. Then, the container may transmit the data to another electronic device for further review (step 907). Generally, the data is transmitted across a wireless communication channel established between the container and the other electronic device. However, the container may be able to transmit data to the other electronic device via a wired communication channel.

Figure 10:
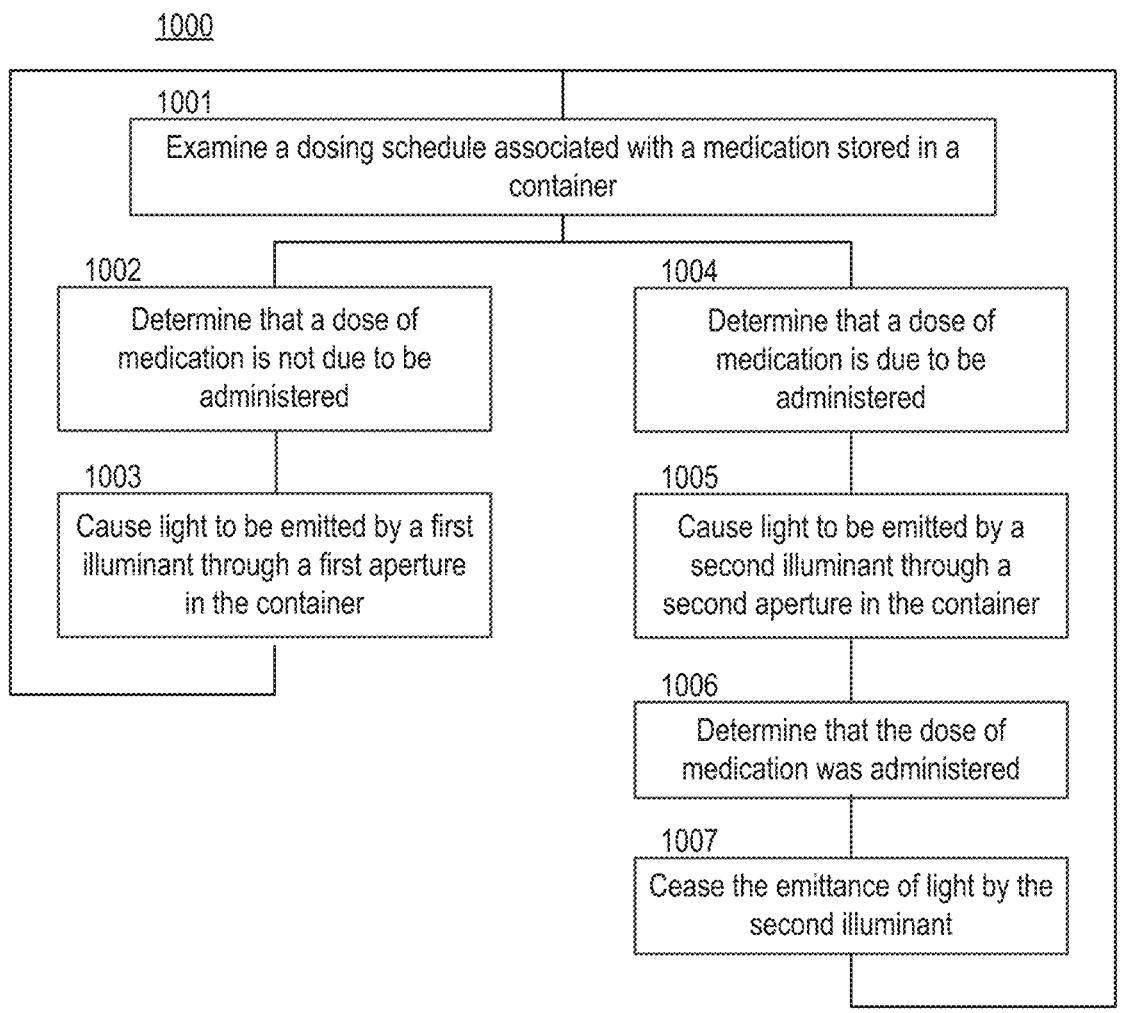
FIG. 10 depicts a flow diagram of a process for selectively driving multiple illuminants to indicate whether medication in a container is due to be administered.

FIG. 10 depicts a flow diagram of a process 1000 for selectively driving multiple illuminants to indicate whether medication in a container is due to be administered. Step 1001 of FIG. 10 may be substantially similar to step 901 of FIG. 9. Here, however, the container includes multiple illuminants that can be driven to convey different instructions related to administrations of the medication.

For example, in some instances, the container will determine that a dose of medication is not due to be administered (step 1002). In such instances, the container can cause light to be emitted by a first illuminant through a first aperture in the container (step 1003). For example, the first illuminant may be driven such that light is emitted through the first aperture on a periodic basis. The first aperture may be in a shape that helps convey that the medication should not be administered. For example, the first aperture may be an x-shaped aperture as shown in FIGS. 7-8. Additionally or alternatively, the first illuminant may be selected such that the emitted light helps convey that the medication should not be administered. For example, the first illuminant may emit red light to indicate that no further action should be taken by the individual.

In other instances, the container will determine that a dose of medication is due to be administered (step 1004). In such instances, the container can cause light to be emitted by a second illuminant through a second aperture in the container (step 1005). For example, the second illuminant may be driven such that light is emitted through the second aperture on a periodic basis. The second aperture may be in a shape that helps convey that the medication should be administered. For example, the second aperture may a check-shaped aperture as shown in FIGS. 7-8. Additionally or alternatively, the second illuminant may be selected such that the emitted light helps convey that the medication should be administered. For example, the second illuminant may emit green light to indicate that further action should be taken by the individual.

Thereafter, the container may determine that the dose was administered (step 1006). Step 1006 of FIG. 10 may be substantially similar to step 904 of FIG. 9. In response to determining that the dose of medication was administered, the container may cease driving the second illuminant so that light is no longer emitted through the second aperture (step 1007). Alternatively, the container may drive the second illuminant such that light is continuously emitted through the second aperture for a given amount of time (e.g., 5, 10, 15, or 30 seconds).

Unless contrary to physical possibility, it is envisioned that the steps described above may be performed in various sequences and combinations. For example, the process 1000 of FIG. 10 could be performed periodically so that some time elapses between changes in state. During these intervals of time, the container may not cause any of its illuminants to produce light. As another example, the process 1000 of FIG. 10 may be performed continuously so that either the first illuminant or the second illuminant is driven at any given point in time. This ensures that the individual can readily comprehend whether medication should be administered with a quick glance at the container.

Other steps may also be included in some embodiments. For example, some embodiments of the container include a third illuminant in addition to the first and second illuminants. In such embodiments, the container may selectively drive the third illuminant to convey whether adherence data has been successfully transmitted, whether a communication channel has been successfully established, etc.

Processing System

Figure 11:
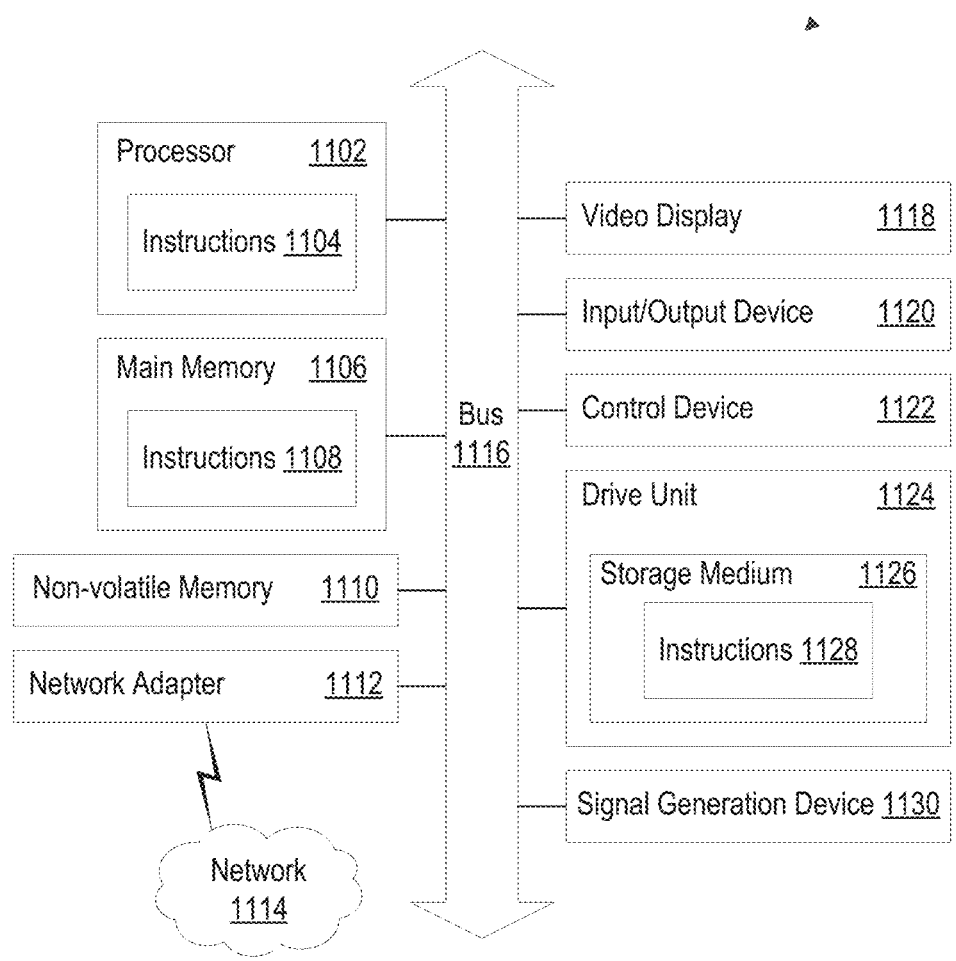
FIG. 11 is a block diagram illustrating an example of a processing system in which at least some operations described herein can be implemented.

FIG. 11 is a block diagram illustrating an example of a processing system 1100 in which at least some operations described herein can be implemented. For example, some components of the processing system 1100 may be hosted on a container (e.g., container 200 of FIG. 2). As another example, some components of the processing system 1100 may be hosted on an electronic device connected to a container across a network.

The processing system 1100 may include one or more central processing units ("processors") 1102, main memory 1106, non-volatile memory 1110, network adapter 1112 (e.g., network interface), video display 1118, input/output devices 1120, control device 1122 (e.g., keyboard and pointing devices), drive unit 1124 including a storage medium 1126, and signal generation device 1130 that are communicatively connected to a bus 1116. The bus 1116 is illustrated as an abstraction that represents one or more physical buses and/or point-to-point connections that are connected by appropriate bridges, adapters, or controllers. The bus 1116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1100 may share a similar computer processor architecture as that of a desktop computer, tablet computer, personal digital assistant (PDA), mobile phone, game console, music player, wearable electronic device (e.g., a watch or a fitness tracker), network-connected ("smart") device (e.g., a television or a home assistant device), virtual/augmented reality systems (e.g., a head-mounted display), or another electronic device capable of executing a set of instructions (sequential or otherwise) that specify action(s) to be taken by the processing system 1100.

While the main memory 1106, non-volatile memory 1110, and storage medium 1126 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1128. The term "machine-readable medium" and "storage medium" shall also be taken to include any medium that is capable of storing, encoding, or carrying a set of instructions for execution by the processing system 1100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1104, 1108, 1128) set at various times in various memory and storage devices in a computing device. When read and executed by the one or more processors 1102, the instruction(s) cause the processing system 1100 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually carry out the distribution.

Further examples of machine-readable storage media, machine-readable media, or computer-readable media include recordable-type media such as volatile and non-volatile memory devices 1110, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1112 enables the processing system 1100 to mediate data in a network 1114 with an entity that is external to the processing system 1100 through any communication protocol supported by the processing system 1100 and the external entity. The network adapter 1112 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1112 may include a firewall that governs and/or manages permission to access/proxy data in a computer network. The firewall may also track varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A container comprising:
a durable housing in which a bulk supply of medication is stored;
a first illuminant arranged beneath a first aperture having a first shape that is formed in the durable housing;
a second illuminant arranged beneath a second aperture having a second shape different than the first shape that is formed in the durable housing;
a third illuminant arranged beneath a third aperture having a third shape different than the first and second shapes that is formed in the durable housing; and
a processor configured to—
examine a dosing schedule associated with the medication,
in response to a determination that a dose of the medication is due to be administered,
cause light to be emitted through the first aperture by the first illuminant,
in response to a determination that the dose of the medication is not due to be administered,
cause light to be emitted through the second aperture by the second illuminant, and
in response to a determination that the dose of the medication was administered within a given preceding amount of time,
cause light to be emitted through the third aperture by the third illuminant.

2. The container of claim 1, wherein the durable housing includes:
a structural body having a cavity defined therein for storing the bulk supply of the medication, and
a cap designed to enclose the cavity when secured to the structural body.

3. The container of claim 2, wherein the first and second apertures are formed in the structural body.

4. The container of claim 2, wherein the first and second apertures are formed in the cap.

5. The container of claim 1, wherein the dosing schedule is stored in a memory accessible to the processor across a network.

6. The container of claim 1, further comprising:
a clock module configured to generate a clock signal.

7. The container of claim 6, wherein the determinations are made by comparing the clock signal to the dosing schedule.

8. The container of claim 1, wherein the first and second illuminants are configured to emit light of different colors.

9. The container of claim 1, wherein the first and second illuminants are light-emitting diodes.

10. A method comprising:
examining a dosing schedule associated with a medication stored in a network-connected container;
in response to a determination that a dose of the medication is due to be administered,
causing light to be periodically emitted by a first illuminant through a first aperture having a first shape that is formed in the network-connected container;
in response to a determination that the dose of the medication is not due to be administered,
causing light to be periodically emitted by a second illuminant through a second aperture having a second shape different than the first shape that is formed in the network-connected container;
in response to a determination that an administration of the dose of the medication occurred within a given preceding amount of time,
causing light to be emitted by a third illuminant through a third aperture having a third shape different than the first and second shapes that is formed in the network-connected container;
recording data related to the administration of the dose of the medication; and
transmitting the data to an electronic device across a network.

11. The method of claim 10, wherein the first and second illuminants periodically emit light at different frequencies.

12. A container comprising:
a durable housing in which a bulk supply of medication is stored;
a first illuminant configured to emit light within a first range of the visible electromagnetic spectrum,
wherein the first illuminant is arranged beneath a first aperture in the durable housing that has a first shape;
a second illuminant configured to emit light within a second range of the visible electromagnetic spectrum,
wherein the second illuminant is arranged beneath a second aperture in the durable housing that has a second shape different than the first shape;
a third illuminant configured to emit light within a third range of the visible electromagnetic spectrum,
wherein the third illuminant is arranged beneath a third aperture in the durable housing that has a third shape different than the first and second shapes; and
a processor configured to—
in response to a determination that a dose of the medication is due to be administered,
selectively cause light to be emitted through the first aperture,
in response to a determination that another dose of the medication is not due to be administered,
selectively cause light to be emitted through the second aperture, and
in response to a determination that the dose of the medication was administered within a given preceding amount of time, selectively cause light to be emitted through the third aperture.

13. The container of claim 1, wherein the first shape is configured to indicate an approval of proceeding with administration of the medication, and wherein the second shape is configured to indicate a disapproval of proceeding with administration of the medication.

14. The container of claim 1, wherein the first shape is configured to convey an instruction to administer the medication, and wherein the second shape is configured to convey an instruction to refrain from administering the medication.

15. The container of claim 1, wherein the first illuminant is configured to emit light of a first color that conveys an instruction to administer the medication, and wherein the second illuminant is configured to emit light of a second color, different than the first color, that conveys an instruction to refrain from administering the medication.

\* \* \* \* \*